United States Patent [19]

Henkelmann et al.

[11] Patent Number: 5,739,398
[45] Date of Patent: Apr. 14, 1998

[54] PREPARATION OF N-ALKENYLUREAS

[75] Inventors: Jochem Henkelmann, Mannheim; Marc Heider, Neustadt; Thomas Rühl, Frankenthal, all of Germany

[73] Assignee: BASF Aktiengesellschaft, Ludwigshafen, Germany

[21] Appl. No.: 675,585

[22] Filed: Jul. 3, 1996

[30] Foreign Application Priority Data

Jul. 6, 1995 [DE] Germany ............... 195 24 619.5

[51] Int. Cl.⁶ ............................................. C07C 275/20
[52] U.S. Cl. ......................... 564/58; 564/32; 564/47; 564/48; 564/49; 564/57; 564/61; 564/62
[58] Field of Search ........................ 564/47, 48, 49, 564/57, 58, 61, 32, 62

[56] References Cited

U.S. PATENT DOCUMENTS

| | | | |
|---|---|---|---|
| 2,541,152 | 12/1951 | Cairns | 260/38.3 |
| 3,919,225 | 11/1975 | Arnold et al. | 260/251 |
| 4,981,973 | 1/1991 | Murray et al. | 548/229 |
| 5,155,253 | 10/1992 | Murray et al. | 560/225 |

FOREIGN PATENT DOCUMENTS

A-911017  5/1954  Germany.

OTHER PUBLICATIONS

Hvala et.al., Vestn. Slov. Kem. Drug., 36(3), pp. 305–323, 1989.
Ledvina et.al., Coll. Czechoslovak Chem. Commun., 47, pp. 676–688, 1982.
Schildberg et al, "Chemische Zuendung von Acetylen...", Chem. Ing. Tech. 66 (1994), pp. 1389–1392.
Crawshaw et al, "The Preparation and Polymerization of N,N'–Divinylureas", J. Macromol. Sci.,–Chem., A5(1), pp. 51–62 (1971).

*Primary Examiner*—Shailendra Kumar
*Attorney, Agent, or Firm*—John H. Shurtleff

[57] ABSTRACT

A process for preparing N-alkenylureas of the general formula I

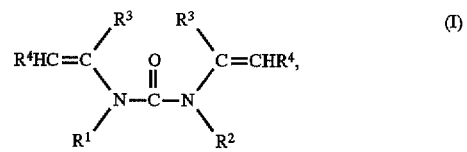

where $R^1$ and $R^2$ are hydrogen, $C_1$- to $C_{40}$-alkyl, $C_2$- to $C_{40}$-alkenyl, $C_3$- to $C_{20}$-cycloalkyl, $C_4$- to $C_{20}$-alkylcycloalkyl, $C_4$- to $C_{20}$-cycloalkylalkyl, aryl, $C_7$- to $C_{20}$-alkylaryl or $C_7$- to $C_{20}$-aralkyl, or aryl, $C_7$- to $C_{20}$-alkylaryl or $C_7$- to $C_{20}$-aralkyl which are mono- to pentasubstituted by $C_1$- to $C_8$-alkyl, $C_1$- to $C_8$-alkoxy or halogen, together are a $C_2$- to $C_{10}$-alkylene chain which is unsubstituted or mono- to hexasubstituted by $C_1$- to $C_8$-alkyl, and $R^3$ and $R^4$ are hydrogen or $C_1$- to $C_8$-alkyl, by reaction of ureas of the general formula II

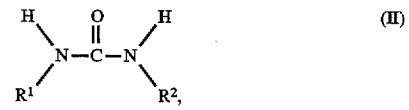

where $R^1$ and $R^2$ have the abovementioned meanings, with an alkenyl carboxylate of the general formula III

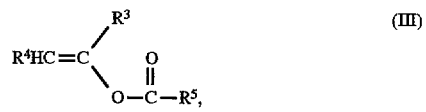

where $R^3$ and $R^4$ have the abovementioned meanings and $R^5$ is hydrogen, $C_1$- to $C_{40}$-alkyl, $C_3$- to $C_{20}$-cycloalkyl, $C_4$- to $C_{20}$-alkylcycloalkyl, aryl, $C_7$- to $C_{20}$-alkylaryl, $C_7$- to $C_{20}$-aralkyl, or aryl or $C_7$- to $C_{20}$-aralkyl which is mono- to trisubstituted by $C_1$- to $C_8$-alkyl, at from 0° to 180° C. and from 0.01 to 10 bar, by carrying out the reaction in the presence of a base is described.

10 Claims, No Drawings

PREPARATION OF N-ALKENYLUREAS

The present invention relates to a novel process for preparing N-alkenylureas by reaction of ureas with an alkenyl carboxylate at elevated temperatures in the presence of a base.

The preparation of divinylureas by reaction of the ureas with acetylene is described in U.S. Pat. No. 2,541,152 and DE-A-911 017.

Working with acetylene requires a large industrial outlay with regard to acetylene availability and safe working with acetylene. Attention is particularly to be given to the safe conduct of the reaction, as the catalyst potassium hydroxide used for the reaction of imidazoles with acetylene can induce decomposition of acetylene in the reaction system. Recent investigations by Schildberg et al. have shown this (Chem. Ing. Tech. 66 (1994) 1389 to 1392).

J. Macromol. Sci., Chem. (1971), 5, pages 51–62 discloses a multi-step acetylene-free synthesis by conversion of the ureas to the disodium salts, reaction to give the bis(β-dimethylaminoethyl) derivatives and cleavage to give the divinyl derivatives by Cope elimination or Hofmann degradation. This process is involved and industrially unsuitable.

It is therefore an object of the present invention to remedy the abovementioned disadvantages.

We have found that this object is achieved by a novel and improved process for preparing N-alkenylureas of the general formula I

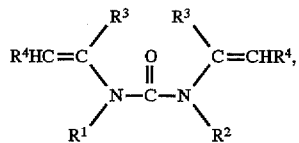 (I)

where $R^1$ and $R^2$ are hydrogen, $C_1$- to $C_{40}$-alkyl, $C_2$- to $C_{40}$-alkenyl, $C_3$- to $C_{20}$-cycloalkyl, $C_4$- to $C_{20}$-alkylcycloalkyl, $C_4$- to $C_{20}$-cycloalkylalkyl, aryl, $C_7$- to $C_{20}$-alkylaryl or $C_7$- to $C_{20}$-aralkyl, or aryl, $C_7$- to $C_{20}$-alkylaryl or $C_7$- to $C_{20}$-aralkyl, which are mono- to pentasubstituted by $C_1$- to $C_8$-alkyl, $C_1$- to $C_8$-alkoxy or halogen, or together are a $C_2$- to $C_{10}$-alkylene chain which is unsubstituted or mono- to hexasubstituted by $C_1$- to $C_8$-alkyl, and $R^3$ and $R^4$ are hydrogen or $C_1$- to $C_8$-alkyl, by reaction of ureas of the general formula II

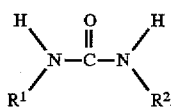 (II)

where $R^1$ and $R^2$ have the abovementioned meanings, with an alkenyl carboxylate of the general formula III

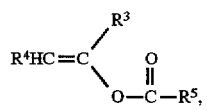 (III)

where $R^3$ and $R^4$ have the abovementioned meanings and $R^5$ is hydrogen, $C_1$- to $C_{40}$-alkyl, $C_3$- to $C_{20}$-cycloalkyl, $C_4$- to $C_{20}$-alkylcycloalkyl, aryl, $C_7$- to $C_{20}$-alkylaryl, $C_7$- to $C_{20}$-aralkyl, or aryl or $C_7$- to $C_{20}$-aralkyl which is mono- to trisubstituted by $C_1$- to $C_8$-alkyl, at from 0° to 180° C. and from 0.01 to 10 bar, which comprises carrying out the reaction in the presence of a base.

The process according to the invention can be carried out as follows:

The ureas II and the alkenyl carboxylates III can be reacted continuously or batchwise in the presence or, preferably, in the absence of the addition of an inert solvent at from 0° to 180° C., preferably 40° to 150° C., particularly preferably 50° to 120° C. and from 0.01 to 10 bar, preferably 0.1 to 2 bar, particularly preferably atmospheric pressure (normal pressure) in the presence of a base, it being possible to mix together the starting materials in any desired sequence. The starting compounds II and III and the base can thus be added, for example, in a stirring vessel and reacted therein. It is also possible to react the starting compounds II and III and the base in a tubular reactor, for example in a trickle or liquid-phase procedure. It has proven advantageous to perform the reaction in a jet nozzle reactor.

Suitable bases are inorganic or organic bases, preferably Brösted bases, eg. carbonates and hydrogen carbonates of the alkali metals and alkaline earth metals such as sodium carbonate, potassium carbonate and sodium hydrogen carbonate, quaternary ammonium carbonates such as tetramethylammonium carbonate, amides such as alkali metal amides, for example sodium amide and potassium amide, hydroxides such as alkali metal hydroxides, for example lithium hydroxide, sodium hydroxide and potassium hydroxide, alkali metal carboxylates such as sodium acetate, alkoxides such as alkali metal alkoxides, for example sodium methoxide, sodium ethoxide, potassium methoxide and potassium tert-butoxide. Potassium hydroxide can also be used together with crown ethers such as 18-crown-6.

Suitable bases are furthermore ammonia, and primary, secondary and tertiary amines, preferably tertiary amines. The amines can carry aliphatic or aromatic radicals, for example trialkylamines such as trioctylamine, ethyldiisopropylamine, diethylisopropylamine, dimethylcyclohexylamine, triethylamine, additionally cyclic amines such as 2,2,6,6-tetramethylpiperidine, 1,4-diazabicyclo[2.2.2]octane, 1,8-diazabicyclo[5.4.0]undec-7-ene, amines carrying aliphatic and aromatic radicals, such as 1,8-bis (dimethylamino)naphthalene and 4-N,N-dimethylaminopyridine and heterocyclic amines such as N-alkylimidazoles and N-arylimidazoles. Amides such as dialkylcarboxamides, eg. dibutylformamide, are furthermore suitable. The process according to the invention can also be carried out in the presence of basic ion exchangers which generally consist of sulfonated styrene/divinylbenzene copolymers such as Amberlite®, Lewatit® and Puralit®, and in the presence of basic zeolites such as hydrotalcite.

The molar ratio of alkenyl carboxylate III to the urea II is generally from 0.1:1 to 10:1, preferably 0.9:1 to 5:1, particularly preferably 2:1 to 2.2:1.

The molar ratio of base to the urea II is generally from 0.1:1 to 10:1, preferably 0.2:1 to 4:1, particularly preferably 0.2:1 to 2:1.

Suitable inert solvents are, for example, aprotic solvents, eg. ethers such as tetrahydrofuran, aromatic hydrocarbons such as toluene and xylene, ketones such as acetone, furthermore acetonitrile, hexamethylphosphoramide, sulfolane, dimethyl sulfoxide, ureas such as N,N'-dimethylethyleneurea, N,N'-dimethylpropyleneurea and tetrabutylurea. The amount is generally from 5 to 300% by weight, preferably 10 to 100% by weight, particularly preferably 10 to 30% by weight, based on the total mixture.

Generally, the reaction is complete after from 5 minutes to 8 hours.

The reaction mixture thus obtained can be worked up in a manner known per se. Generally, the N-alkenylurea I is removed by distillation. The distillation bottom can be treated with alkalis such as sodium hydroxide solution to release the organic bases from the salts formed in the reaction. If a 4-N,N-dialkylaminopyridine is employed in the reaction according to the invention, the acids formed and the amine can be separated from one another even without treatment with bases. The bases employed can then be isolated by extraction or distillation. If, in the reaction according to the invention, readily volatile salt-like compounds such as formates of tertiary ammonium compounds are formed, these can also be worked up by distillation and converted into the corresponding amines. The bases separated off in each case can be fed back into the reaction.

The substituents $R^1$, $R^2$, $R^3$, $R^4$ and $R^5$ in the compounds I, II and III have the following meanings:

$R^1$, $R^2$, $R^3$, $R^4$ and $R^5$ are
hydrogen, $R^1$, $R^2$ and $R^5$ are
$C_3$- to $C_{20}$-cycloalkyl, preferably $C_3$- to $C_{12}$-cycloalkyl, particularly preferably $C_5$- to $C_8$-cycloalkyl such as cyclopentyl, cyclohexyl, cycloheptyl and cyclooctyl, $C_4$- to $C_{20}$-alkylcycloalkyl, preferably $C_4$- to $C_{12}$-alkylcycloalkyl, particularly preferably $C_5$- to $C_{10}$-alkylcycloalkyl, aryl such as phenyl, 1-naphthyl and 2-naphthyl, preferably phenyl, $C_7$- to $C_{20}$-alkylaryl, preferably $C_7$- to $C_{16}$-alkylaryl, preferably $C_7$- to $C_{12}$-alkylphenyl such as 2-methylphenyl, 3-methylphenyl, 4-methylphenyl, 2-ethylphenyl, 3-ethylphenyl and 4-ethylphenyl, $C_7$- to $C_{20}$-aralkyl, preferably $C_7$- to $C_{16}$-aralkyl, preferably $C_7$- to $C_{12}$-phenalkyl such as phenylmethyl, 1-phenylethyl and 2-phenylethyl, $R^1$ and $R^2$ are
$C_1$- to $C_{40}$-alkyl, preferably $C_1$- to $C_{12}$-alkyl, particularly preferably $C_1$- to $C_8$-alkyl such as methyl, ethyl, n-propyl, isopropyl, n-butyl, isobutyl, sec-butyl, tert-butyl, n-pentyl, isopentyl, n-hexyl, isohexyl, n-heptyl, isoheptyl, n-octyl and isooctyl, $C_2$- to $C_{40}$-alkenyl, preferably $C_2$- to $C_{12}$-alkenyl, particularly preferably $C_2$- to $C_8$-alkenyl such as vinyl and propenyl, $C_4$- to $C_{20}$-cycloalkylalkyl, preferably $C_4$- to $C_{12}$-cycloalkylalkyl, particularly preferably $C_5$- to $C_{10}$-cycloalkylalkyl, aryl which is mono- to pentasubstituted by $C_1$- to $C_8$-alkyl, $C_1$- to $C_8$-alkoxy or halogen, preferably phenyl which is mono- to trisubstituted by $C_1$- to $C_8$-alkyl, $C_1$- to $C_8$-alkoxy or halogen, $C_7$- to $C_{20}$-alkylaryl which is mono- to pentasubstituted by $C_1$- to $C_8$-alkyl, $C_1$- to $C_8$-alkoxy or halogen, preferably $C_7$- to $C_{16}$-alkylphenyl which is mono- to trisubstituted by $C_1$- to $C_8$-alkyl, $C_1$- to $C_8$-alkoxy or halogen, $C_7$- to $C_{20}$-aralkyl which is mono- to pentasubstituted by $C_1$- to $C_8$-alkyl, $C_1$- to $C_8$-alkoxy or halogen, preferably $C_7$- to $C_{16}$-phenalkyl which is mono- to trisubstituted by $C_1$- to $C_8$-alkyl, $C_1$- to $C_8$-alkoxy or halogen, together a $C_2$- to $C_{10}$-alkylene chain, preferably a $C_2$- to $C_8$-alkylene chain, particularly preferably $—(CH_2)_2—$, $—(CH_2)_3—$, $—(CH_2)_4—$ and $—(CH_2)_5—$, in particular $—(CH_2)_2—$ and $—(CH_2)_3—$, together a $C_2$- to $CH_{10}$-alkylene chain which is unsubstituted or mono- to hexasubstituted by $C_1$- to $C_8$-alkyl, preferably together a $C_2$- to $C_5$-alkylene chain which is unsubstituted or mono- to trisubstituted by $C_1$- to $C_4$-alkyl, $R^3$ and $R^4$ are
$C_1$- to $C_8$-alkyl, preferably $C_1$- to $C_4$-alkyl such as methyl, ethyl, n-propyl, isopropyl, n-butyl, isobutyl, sec-butyl and tert-butyl, particularly preferably methyl and ethyl, $R^5$ is
$C_1$- to $C_{40}$-alkyl, preferably $C_1$- to $C_{20}$-alkyl, particularly preferably methyl, ethyl, n-propyl, isopropyl, n-butyl, tert-butyl, n-pentyl, n-hexyl, n-heptyl, n-octyl, n-decyl, n-dodecyl and n-octadecyl, aryl which is mono- to trisubstituted by $C_1$- to $C_8$-alkyl, preferably phenyl which is mono- to trisubstituted by $C_1$- to $C_4$-alkyl, such as 2-methylphenyl, $C_7$- to $C_{20}$-aralkyl which is mono- to trisubstituted by $C_1$- to $C_8$-alkyl, preferably $C_7$- to $C_{16}$-phenalkyl which is mono- to trisubstituted by $C_1$- to $C_4$-alkyl.

Alkenyl carboxylates III which may preferably be mentioned are: vinyl formate, vinyl acetate, vinyl propionate, vinyl stearate (vinyl octadecanoate), vinyl pivalate (vinyl 2,2-dimethylpropionate) and vinyl 4-tert-butylbenzoate.

The alkenyl carboxylates III are commercially available or can be prepared by known methods, for example by addition of carboxylic acids to acetylene or by acetoxylation of ethylene (Industrielle Organische Chemie (Industrial Organic Chemistry), 2nd edition, 1978, Verlag Chemie, pages 217 to 223).

Ureas II which may preferably be mentioned are: ethylene- and propyleneurea.

These compounds are also commercially available or obtainable by known methods.

The products of the formula I are sought-after intermediates eg. for crosslinked polymers (DE-A-35 43 348).

EXAMPLES

Example 1

N,N'-Divinylpropyleneurea 15 g (0.15 mol) of propyleneurea and 12 g (0.1 mol) of 4-N,N-dimethylaminopyridine were initially introduced, heated to 95° C., 25.8 g (0.26 mol) of vinyl propionate were added dropwise in the course of 15 minutes and the mixture was refluxed for 5.5 hours.

After working up by distillation, 20.3 g (89%) of N,N'-divinylpropleneurea were obtained; b. p.: . . . to . . . °C.

Example 2

N,N'-Divinylethyleneurea 43 g (0.5 mol) of ethyleneurea and 30.5 g (0.25 mol) of 4-N,N-dimethylaminopyridine were initially introduced in 100 g of toluene, heated to 100° C., 110 g (1.1 mol) of vinyl propionate were added dropwise in the course of 30 minutes and the mixture was refluxed for 5 hours.

After working up by distillation, 63.6 g (91%) of N,N'-divinylethyleneurea were obtained; b. p.:

We claim:

1. A process for preparing N-alkenylureas of the formula I $$R^4HC=C\begin{matrix}R^3\\ \diagup\end{matrix}\begin{matrix}\\ \diagdown\end{matrix}\begin{matrix}O\\ \|\\ N-C-N\end{matrix}\begin{matrix}R^3\\ \diagdown\\ \diagup\end{matrix}C=CHR^4, \qquad (I)$$
$$\begin{matrix}R^1\end{matrix}\qquad\qquad\begin{matrix}R^2\end{matrix}$$

where $R^1$ and $R^2$ are hydrogen, $C_1$- to $C_{40}$-alkyl, $C_2$- to $C_{40}$-alkenyl, $C_3$- to $C_{20}$-cycloalkyl, $C_4$- to $C_{20}$- alkylcycloalkyl, $C_4$- to $C_{20}$-cycloalkylalkyl, aryl, $C_7$- to $C_{20}$-alkylaryl or $C_7$- to $C_{20}$-aralkyl, or aryl, $C_7$- to $C_{20}$-alkylaryl or $C_7$- to $C_{20}$-aralkyl which are mono- to pentasubstituted by $C_1$- to $C_8$-alkyl, $C_1$- to $C_8$-alkoxy or halogen, or together are a $C_2$- to $C_{10}$-alkylene chain which is unsubstituted or mono- to hexasubstituted by $C_1$- to $C_8$-alkyl, and $R^3$ and $R^4$ are hydrogen or $C_1$- to $C_8$-alkyl, which comprises reacting ureas of the formula II

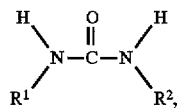 (II)

where $R^1$ and $R^2$ have the abovementioned meanings, with an alkenyl carboxylate of the formula III

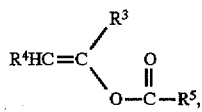 (III)

where $R^3$ and $R^4$ have the abovementioned meanings and $R^5$ is hydrogen, $C_1$- to $C_{40}$-alkyl, $C_3$- to $C_{20}$-cycloalkyl, $C_4$- to $C_{20}$-alkylcycloalkyl, aryl, $C_7$- to $C_{20}$-alkylaryl, $C_7$- to $C_{20}$-aralkyl, or aryl or $C_7$- to $C_{20}$-aralkyl which is mono- to trisubstituted by $C_1$- to $C_8$-alkyl, at from 0° to 180° C. and from 0.01 to 10 bar, and in the presence of a base.

2. A process for preparing N-alkenylureas as claimed in claim 1, wherein $R^3$ is hydogen.

3. A process as claimed in claim 1, wherein $R^1$ and $R^2$ independently are hydrogen or $C_1$- to $C_{20}$-alkyl or, when taken together, represent a $C_1$- to $C_{12}$-alkylene chain which is unsubstituted or mono- to trisubstituted by $C_1$- to $C_4$-alkyl.

4. A process as claimed in claim 1, wherein $R^1$ and $R^2$ independently are $C_1$- to $C_{12}$-alkyl or, when taken together, represent a $C_2$- to $C_5$-alkylene chain.

5. A process as claimed in claim 1, wherein the reaction is carried out at from 40° to 150° C.

6. A process as claimed in claim 1, wherein the reaction is carried out at from 50° to 120° C.

7. A process as claimed in claim 1, wherein the reaction is carried out at from 0.1 to 2 bar.

8. A process as claimed in claim 1, wherein the reaction is carried out at atmospheric pressure.

9. A process as claimed in claim 1 wherein $R^3$ and $R^4$ are hydrogen.

10. A process as claimed in claim 1 wherein the reactant of the formula III is selected from the group consisting of vinyl acetate and vinyl propionate.

* * * * *